US012592307B2

(12) United States Patent
Gaillardon et al.

(10) Patent No.: US 12,592,307 B2
(45) Date of Patent: Mar. 31, 2026

(54) COMPUTERIZED SYSTEM AND METHOD FOR THE DETERMINATION OF A DRUG DOSAGE, AND COMPUTER PROGRAM

(71) Applicant: DIABELOOP, Grenoble (FR)

(72) Inventors: Gilles Gaillardon, Grenoble (FR); Mathieu Cattelan, Grenoble (FR)

(73) Assignee: DIABELOOP, Grenoble (FR)

( * ) Notice: Subject to any disclaimer, the term of this patent is extended or adjusted under 35 U.S.C. 154(b) by 650 days.

(21) Appl. No.: 18/148,920

(22) Filed: Dec. 30, 2022

(65) Prior Publication Data

US 2023/0317234 A1     Oct. 5, 2023

(30) Foreign Application Priority Data

Dec. 31, 2021    (EP) ..................................... 21218463

(51) Int. Cl.
*G16H 20/17*         (2018.01)
*A61M 5/172*        (2006.01)

(52) U.S. Cl.
CPC .......... *G16H 20/17* (2018.01); *A61M 5/1723* (2013.01); *A61M 2205/3584* (2013.01); *A61M 2205/52* (2013.01)

(58) Field of Classification Search
None
See application file for complete search history.

(56) References Cited

U.S. PATENT DOCUMENTS

| | | | |
|---|---|---|---|
| 10,278,580 B2 | 5/2019 | Brister et al. | |
| 11,881,295 B2 * | 1/2024 | Hanson | .................. G16H 20/10 |
| 2018/0200440 A1 * | 7/2018 | Mazlish | ................ G16H 20/17 |
| 2018/0353698 A1 | 12/2018 | Saint et al. | |
| 2019/0175833 A1 | 6/2019 | Sjolund et al. | |
| 2019/0298920 A1 | 10/2019 | Haider et al. | |

FOREIGN PATENT DOCUMENTS

WO      WO2020/214981 A1    10/2020

OTHER PUBLICATIONS

Extended European Search Report dated May 24, 2022 for European Application No. 21218463.4.

* cited by examiner

*Primary Examiner* — Manuel A Mendez

(57)                    ABSTRACT

A computerized system for the determination of a drug dosage comprises a dose determination module which determines a possible drug dosage, a security module which determines whether a security threshold is triggered, a notification module which, when the security module determines that a security threshold is triggered, issues a user notification, a communication module which receives drug dosage data from a drug dispensing device. The notification module allows the user to acknowledge the notification independently of received drug dosage data.

8 Claims, 6 Drawing Sheets

[Fig. 1]
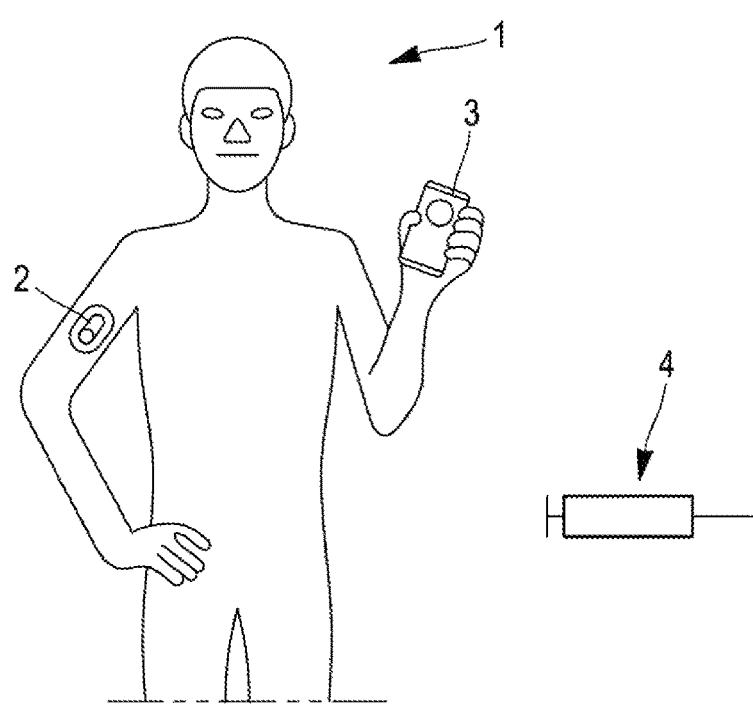
[Fig. 2]
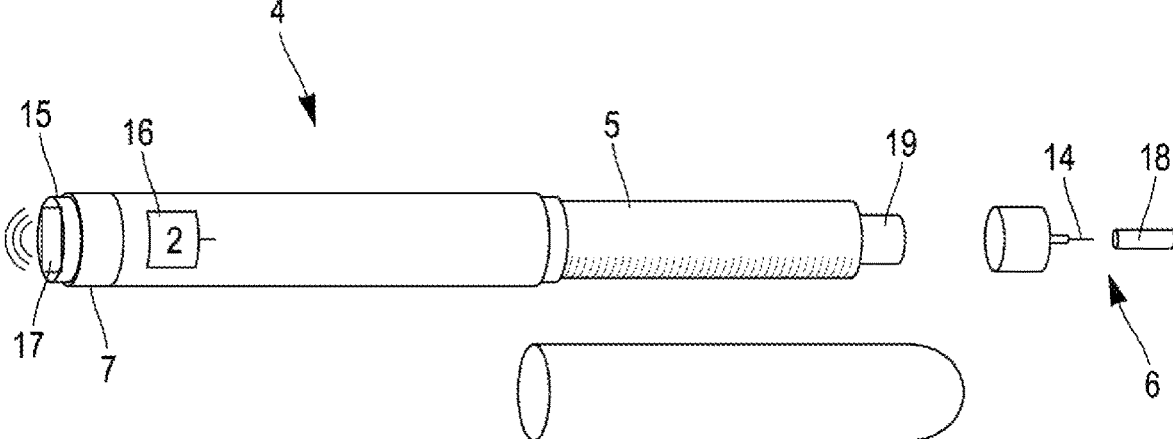

[Fig. 3]
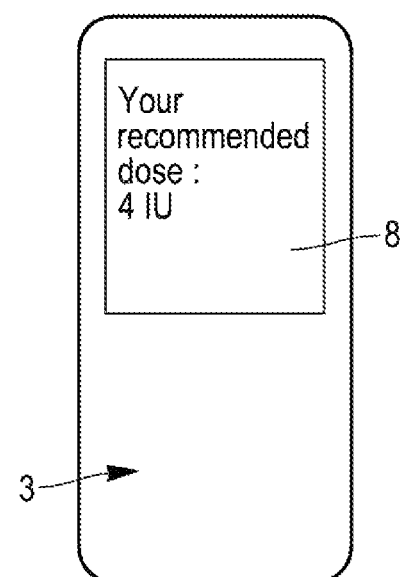
[Fig. 4]
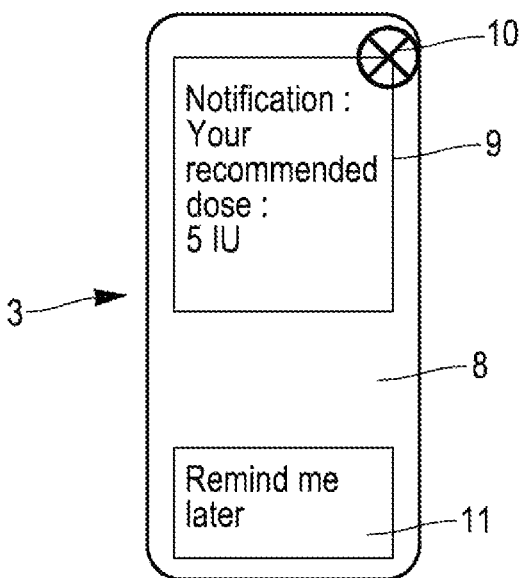

[Fig. 5]
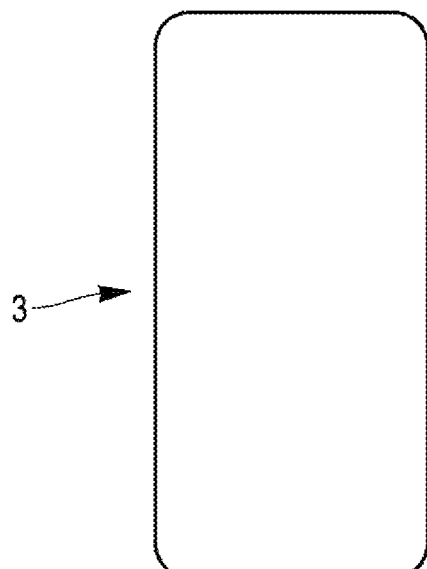
[Fig. 6]
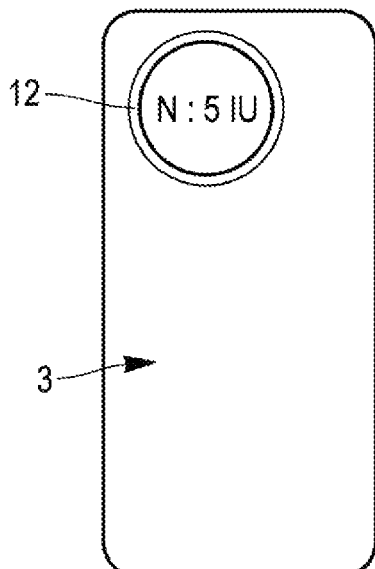

[Fig. 7]
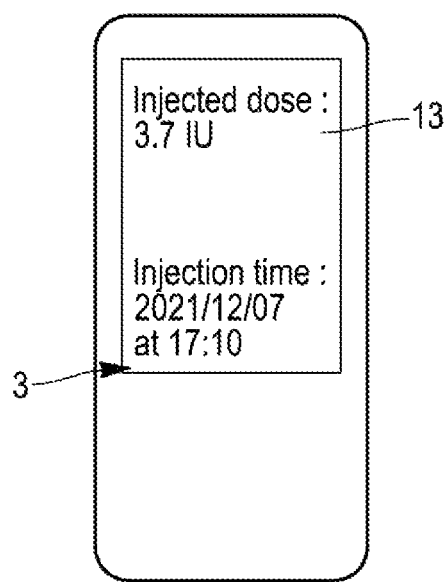
[Fig. 8]
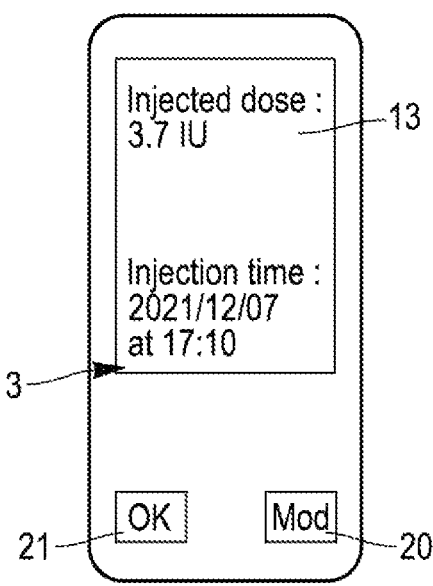

[Fig. 9]
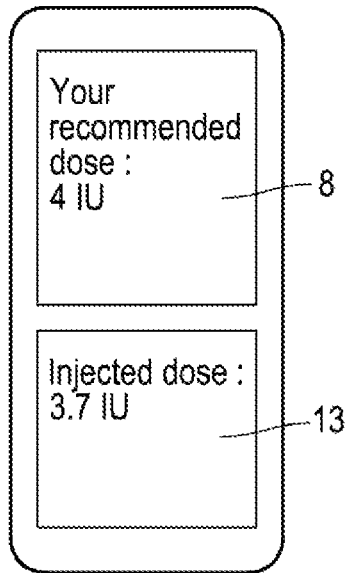
[Fig. 10]
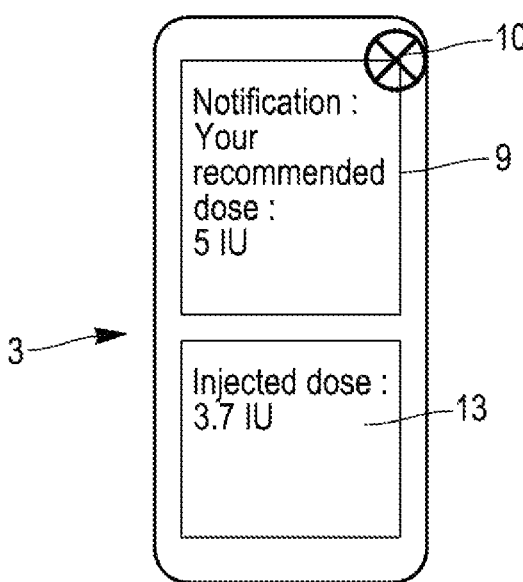

[Fig. 11]
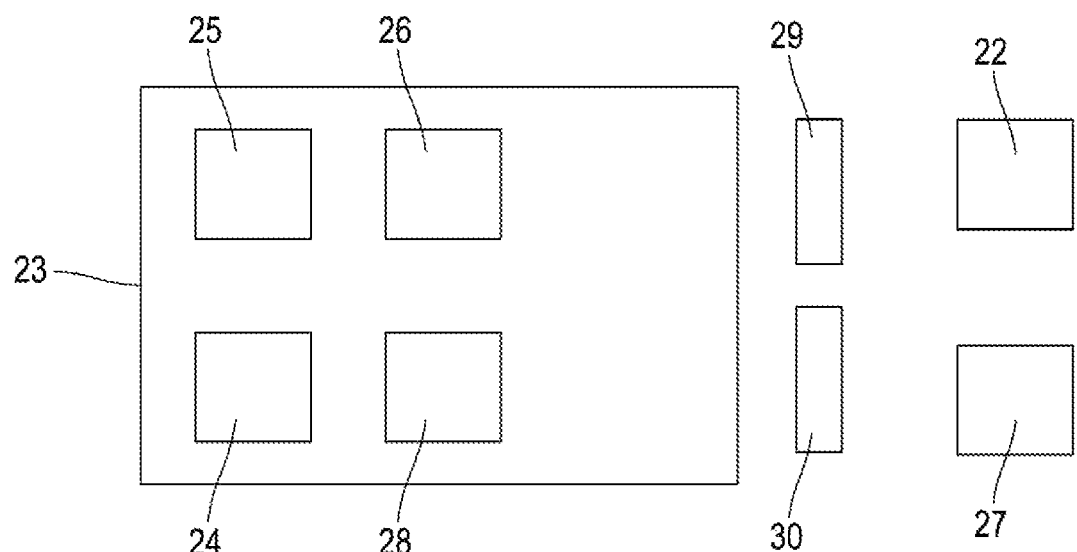

COMPUTERIZED SYSTEM AND METHOD FOR THE DETERMINATION OF A DRUG DOSAGE, AND COMPUTER PROGRAM

FIELD OF THE INVENTION

The present invention relates to computerized systems and methods for the determination of a drug dosage.

BACKGROUND OF THE INVENTION

More specifically, the invention relates to a computerized system for the determination of a drug dosage.

A user may need to determine a suitable quantity of drug. In particular, for some conditions, the user may need to determine a suitable quantity of drug to be dispensed to oneself, without help of a doctor or practitioner.

One example of the invention is for example in the field of diabetes. The user may need to determine a quantity of insulin to be dispensed to him/herself in order to regulate his/her blood glucose. This determination takes into account a plurality of factors. Insulin will be typically dispensed in fluid form intradermally.

Document WO 2020/214,981 is an example in which a user uses a bolus dose calculator in order to determine a dose of insulin to be injected. The output of the dose calculator is a dose recommendation displayed on a user interface. The document suggests the dose recommendation be displayed until the user injects that dose. However, various options are presented in order to dismiss or remove the dose recommendation from the user interface screen, based on elapsed time or sum value of the doses. This system relies heavily on the habit of the patient to regularly request a bolus dose calculation.

Document US 2018/353,698 describes an insulin pen system wherein a learning dose calculator module is adapted to determine a dose of insulin for injection to the patient. The system comprises an application running on a smartphone with a display screen, which may show a real-time display of the currently calculated glucose correction dose. In some implementations, an alarm is generated based on the output of the learning dose calculator module when the calculated dose of at least a certain amount of medicine is needed to get back to the target glucose value. However, the interaction of the patient with the terminal in case of alarms is not described. There is a risk that alarms would unduly remain displayed, which is troublesome for the patient and may lead to misdistributions.

The invention thus aims at providing a drug dosage system being able to accompany the user in a safe and efficient way.

BRIEF SUMMARY OF THE INVENTION

Thus, the invention relates to a computerized system for the determination of a drug dosage to be applied to a user, wherein the computerized system comprises:
- a memory storing data comprising at least time-based user metabolite data,
- a processor comprising:
  - a dose determination module adapted to determine a possible drug dosage based on said data and at least one rule associating possible dosages and data,
  - a security module adapted to determine whether said time-based user metabolite data triggers a security threshold,

- a notification module adapted to, when the security module determines that a security threshold is triggered, issue a user notification comprising at least said possible dosage,
- a user interface adapted to interact with the user, comprising:
  - an output module adapted to provide said user notification to the user,
  - an input module adapted to receive information from the user regarding the notification,
- a communication module adapted to receive drug dosage data from a drug dispenser,
- Wherein the notification module is adapted to allow the user to acknowledge the notification through the input module independently of said received drug dosage data.

Thanks to these provisions, the user may treat the drug dosage notification as a notification, independent of whether s/he will actually apply the recommendation by the system. The notification system enables to enhance the security for the user, but enables a large flexibility to be usable by various users with different sensibility to and knowledge of handling diabetes.

According to different aspects, it is possible to provide the one and/or the other of the characteristics below taken alone or in combination.

According to one embodiment, the notification module is adapted to allow the user to acknowledge the notification through the input module even after the communication module receives drug dosage data associated with the notification.

According to one embodiment, the notification module is adapted to issue said notification together with an actuatable window close button, and notification acknowledgement comprises detecting actuation of said window close button.

According to one embodiment, the notification module is adapted to issue said notification together with an actuatable reminder button adapted to, upon actuation, trigger a later notification, and notification acknowledgement comprises detecting actuation of said reminder button.

According to one embodiment, the notification module is adapted, upon actuation of the reminder button, to control display of a substitute window bearing said possible drug dosage.

According to one embodiment, the processor further comprises a query module adapted, when actuated by the user, to provide the user with the most recently possible drug dosage data.

According to another aspect, the invention relates to a computerized method for the determination of a drug dosage to be applied to a user, wherein the computerized method comprises:
- a dose determination module of a processor determines a possible drug dosage based on said data contained in a memory, and comprising at least time-based user metabolite data, and on at least one rule associating possible dosages and data,
- a security module determines whether said time-based user metabolite data triggers a security threshold,
- when the security module determines that a security threshold is triggered, a notification module issues a user notification comprising at least said possible dosage,
- an output module of a user interface adapted to interact with the user provides said user notification to the user,
- an input module of said user interface receives information from the user regarding the notification, a communication module receives drug dosage data from a drug dispenser, the notification module allows the user to acknowledge the notification through the input module independently of said received drug dosage data.

According to another aspect, the invention relates to a computer software comprising instructions which, when the program is executed by a computer, cause the computer to carry out the above method.

BRIEF DESCRIPTION OF THE DRAWINGS

Embodiments of the invention will be described below with reference to the drawings, described briefly below:

FIG. 1 schematically represents a drug dosage system.

FIG. 2 is an exploded view schematically representing a drug dispensing device according to one embodiment.

FIGS. 3-10 schematically represent a front displaying face of terminal.

FIG. 11 schematically represents components of the terminal.

In the drawings, identical references designate identical or similar objects.

DETAILED DESCRIPTION OF THE INVENTION

FIG. 1 shows an example of a drug dosage system 1. The drug dosage system 1 will be described in relation to an application for diabetes. However, other applications of the invention are possible. The drug dosage system 1 comprises a sensing system 2 adapted to measure a parameter of the user. In particular, the sensing system 2 might comprise a wearable, which is worn by the user. In addition, the sensing system 2 is adapted to repeatedly provide a measurement of the parameter of the user. The sensing system 2 may comprise a clock, so that time data is associated with measurement data. Such sensing systems may be called continuous sensing systems. The sensing system may be adapted to perform in vivo measurements. Hence, the measured parameter may be a concentration of a metabolite, such as, for example, glucose.

The sensing system 2 comprises a data communication device adapted to communicate data to a remote system. The data communication device might be adapted to communicate wirelessly, for example using a short-range radio communication corresponding to the Bluetooth® standard at the priority date of the patent application.

The drug dosage system 1 further comprises a terminal 3. As further shown on FIG. 11, the terminal 3 comprises a processor 23 and a memory 22. The terminal 3 comprises a data communication module 27 adapted to communicate data to a remote system. The data communication module 27 might be adapted to communicate wirelessly, for example using a short-range radio communication corresponding to the Bluetooth® standard at the priority date of the patent application. For example, the data communication module 27 of the terminal 3 and the data communication device of the sensing system 2 are compatible with one another, to form a communication system, by which the terminal 3 and the sensing system 2 communicate with one another. In particular, measurement data, and possibly time data, are communicated from the sensing system 2 to the terminal 3, and stored in the memory of the terminal 3.

The terminal 3 may further comprise a user interface. The user interface allows the user to communicate with the processor 23 and/or the memory 22 of the terminal 3. The user interface may comprise one or more among pressbuttons, touch screen, vocal command and speakers, etc . . . . The user interface comprises an output module 30 through which the processor may provide information to the user, and an input module 29 through which the user may provide information to the processor.

The user interface may be designed to enable the user to provide information to the processor. In the specific example of diabetes, the user interface may be used by the user to provide information about meals, such as time of the meal (start time, end time, . . . ), size of the meal (qualitative or quantitative), type of the meal (breakfast, lunch, dinner, snack, . . . ), nutrition characteristics of the meal (fat meal, sweet meal, . . . ). The user interface may be used by the user to provide other information, such as information related to physical exercise (time, intensity, . . . ), or values for parameters of the system.

The user interface may be designed to be able to obtain information from the user. The user interface will for example display a number of screens providing the user with options to be selected, in order to be able to navigate and to enter or retrieve displayed information. A more detailed example will be described below.

As described in more details on FIG. 2, the drug dosage system 1 further comprises a drug dispensing device 4. The drug dispensing device 4 comprises a container 5 with drug. Typically, the container 5 comprises more than one dose of drug, so as to be used a plurality of times. The drug dispensing device 4 further comprises a dispensing system 6 adapted to dispense drug to the user. This comprises for example a needle 14 to be inserted into the body of the user, and a plunger 15 which can be pushed to expel drug from the container 5 through the needle 14 into the user's body.

The drug dispensing device 4 further comprises a setting system 7. The setting system 7 can be set by the user in order to limit the amount of drug which may be injected at a time using the drug dispensing device 4. For example, the setting system 7 may be set by the user at an amount of, for example, 2 units, as shown, and the dispensing system is actuated to dispense drug and is prevented from operating when 2 units have been injected. For example, a settable mechanical stop for the plunger may be used. The drug dispensing device 4 may comprise a window 16 showing the set dose. Other embodiments are possible.

The drug dispensing device 4 further comprises a drug quantity estimation device adapted to estimate the quantity of dispensed drug. For example, the estimation device will be triggered by the actuation of the drug dispensing system 6 for a predetermined time. The estimation device will estimate the quantity of drug leaving the drug dispensing device 4 from the start time to the end time. Quantity of drug might be determined as a mass, a volume, or any other suitable quantity.

For example, the setting system 7 comprises an encoder, so that the position of the setting system with respect to a reference is representative of a quantity of drug to be dispensed. The drug quantity estimation device gathers the information as to the quantity of drug to be dispensed from the encoder. Hence, the quantity of drug may be estimated based on the difference of position of the encoder at the start of the dispensing and at the end of the dispensing.

The drug dispensing device 4 further comprises a data communication device 17 adapted to communicate data to a remote system. The data communication device 17 might be adapted to communicate wirelessly, for example using a short-range radio communication corresponding to the Bluetooth® standard at the priority date of the patent application. For example, the data communication module 27 of the terminal 3 and the data communication device 17 of the drug dispensing device 4 are compatible with one another, to form a second communication system, by which the terminal 3 and the drug dispensing device 4 communicate with one another. In particular, dispensed drug quantity estimation data estimated by the drug quantity estimation device are communicated from the drug dispensing device 4 to the terminal 3, and stored in the memory 22 of the terminal 3.

The drug dispensing device 4 may further comprise other parts such as caps 18, seals 19, . . .

The terminal 3 comprises a controller. The controller comprises a dose determination module 24 adapted to determine a quantity of drug to be dispensed. The controller bases its determination on data entered by the user (such as physiological information and meal and activity information as described above), measurement data received from the sensing system 2, and dispensed drug data received from the drug device 4.

For example, the controller implements predefined rules to determine a quantity of drug to be dispensed based on the above-listed data.

For example, the controller implements a physiological model representing the physiology of the user linking together the above data. For the specific case of diabetes, the controller comprises a model determining a quantity of insulin to be dispensed based at least on measured glucose data, declared meals and physical activity, and history of dispensed insulin.

According to the invention, the controller is repeatedly run in order to estimate an up-to-date value of insulin to be dispensed. This value is a possible drug dosage. In the present text, it is also called a "recommended" dose. However, the dose determination module does not necessarily have access to all necessary information when determining the "recommended" dose. Therefore, the "recommended" dose is only recommended in the light of the information available to the dose determination module. The dose recommendation module does not perform a medical diagnostic.

For example, the controller is run at a pre-set frequency, such as, for example, every few minutes, e.g. every 2 minutes or every 15 minutes. Alternately, or in addition, the controller might be run each time the terminal 3 receives sensor data from the sensing system 2.

At any given time, the user may query the terminal in order to check for the last quantity of drug determined. For example, the user may do this before a meal, or before a time period during which he knows he will be unable to inject drug, for example a car, train, boat or plane travel, a social event (restaurant, cinema, party, . . . ) or else. The terminal 3 offers a dose query module 28 which can be actuated by the user (for example a push button or a vocal command) wanting to know the most recently determined drug dose.

As shown on FIG. 3, the display 8 of the terminal 3 displays the most recently determined recommended dose.

The user then sets the setting system 7 of the drug dispensing device 4 at any value s/he seems suitable. Generally speaking, the user has no obligation to use the exact value provided by the controller. The user may determine to dispense a different quantity because s/he knows what is planned for the rest of the day better than the terminal does. For example, the user knows that he will be unable to dispense drug for the next 12 hours, or that s/he will have a fat meal, or else, and may dispense a quantity larger than recommended.

The exact injected quantity is communicated to the terminal 3 through the second communication system.

In any case, the most recently determined dose remains displayed at the terminal, as shown on FIG. 3, even though drug is being injected, or has just been injected, until a new determination by the controller is run, which takes into account new sensor data and/or new injection data.

According to an example, in addition to the description above, where the user "pulls" drug delivery data from the system 1, the system 1 may also operate in "push" mode where the system 1 determines that it is suitable to inform the user about a quantity of drug to be dispensed. In particular, the processor comprises a security module 25 adapted to determine whether a security threshold is triggered.

In the present example, since dosage determination is performed frequently, for example many times per hour, the security module is adapted to determine whether to notify the user that dispensing drug is recommended.

The security module applies preset rules in order to determine whether to notify the user. The rules are set in order to disturb the user only when necessary. For example, the rules are based on the assessment of a health risk related to the lack of drug. The health risk may be pre-programmed in the security module, and may comprise a trigger based on one or more of the following criteria:

Sensed data is outside of a preset range,

Variation rate of sensed data is outside of a preset range,

Acceleration rate of sensed data is outside of a preset range,

The controller determines a prediction of a value for the sensed data at a future time, based on the input data, and this prediction value is outside a preset range.

The criteria are for example checked each time the controller is run to determine a new drug dispensing recommended data. If the criteria are not met, no notification is provided to the user.

If the criterion, or one of the criteria is met, a notification module 26 notifies the user. For example, the notification module displays a warning message on a display screen of the terminal, as shown on FIG. 4, and displays also the most recently determined drug dispensing recommended data. The terminal 3 may further comprise warning means to warn the user of the issuance of a notification, such as a loudspeaker or a vibrating system.

As can be seen on FIG. 4, the display screen 8 displays a window 9 comprising a display of the recommended value. It provides the user with the option of closing the window through a window close button 10. It may further comprise the option of enabling the user to ask for a reminder, through a reminder button 11. The window close button 10 or the reminder button 11 allows the user to acknowledge the notification to the processor.

If the user does not actuate the window close button 10 nor the reminder button 11, the window remains displayed as shown on FIG. 4.

If the user actuates the window close button 10, the window 9 is removed from the display, as well as the reminder button 11, as shown on FIG. 5. If needed, the user may still access the most recently determined recommendation data as described above in the "pull" mode.

If the user actuates the reminder button 11, the window 8 is removed from the display, and the reminder button 11 as well. Yet, as shown on FIG. 6, an icon or substitute window 12 remains displayed on screen. The icon or substitute window 12 may display the value of the recommended data. After a pre-set time, the user may receive a notification again, as shown on FIG. 4. The pre-set time for the reminder lag might be lower than the time interval between two determinations by the controller. Alternatively, the pre-set time for the reminder lag might be greater than the time interval between two determinations by the controller. In this case, if a new determination is performed before notifying a reminder of the notification, the reminder notification comprises the updated determination in lieu of the previous determination. This is particularly the case when the updated determination is greater than 0, or at least greater than a pre-determined threshold. If the updated determination is 0, or lower than the pre-determined threshold, for example because drug was dispensed meanwhile, and dispensed drug was taken into account for the updated determination, the reminder notification is cancelled and is not displayed. The pre-set time, also called "snooze" time, between two notifications may be set and may be customisable/parametrisable.

In any case, whether the user does not press any of the buttons, presses the window close button 10 or the reminder button 11, if the user injects drug, the value of the quantity of injected drug is transferred to the controller as described above.

Once drug is injected, and the information is communicated to the terminal 3, the display 8 of the terminal 3 shows a window 13 providing the user with the quantity of drug injected, as shown on FIG. 7, as well as injection time. For example, the drug dispensing device comprises an encoder representing the amount of dispensed drug, and the current value of the encoder is repeatedly detected and transmitted to the terminal 3. For example, the encoder is associated to the plunger 15, so that the position of the plunger is monitored. For example, the window 13 is repeatedly updated to display the dispensed amount of drug. According to another example, the end of the drug dispensing is detected at the drug dispensing device, and the amount of dispensed drug is communicated to the terminal 3 at that time. The end of the drug dispensing is for example detected by an end-of-stroke contact of the plunger. This window 13 is displayed for a predetermined amount of time.

According to one embodiment, as shown on FIG. 8, the window 13 may offer the possibility to the user to amend the evaluated dose. The window 13 thus comprises an "amend" button 20 which, when actuated, offers the possibility to the user to modify the estimated dose. This modification may be possible using increasing or decreasing signs to control an increase or decrease of the displayed value, for example by a pre-set value, or access to a keyboard for the user to type in the correction. The window 13 thus comprises a "Validation" button 21 which enables the user to inform the processor of the terminal that the amendment is performed. The "Validation" button may be actuated even if no modification is entered.

According to one embodiment, the terminal 3 will provide access to the amend and validation buttons 20, 21 only in some circumstances, for example depending on the amount of dispensed drug. For example, if the amount of dispensed drug is less than a predetermined threshold, the amend and validation buttons will be displayed to the user. Hence, in case little drug is dispensed, it is possible for the user to amend the amount, in order to take into account a priming dose, for example. It is considered that, for large doses, the impact of the priming dose will be low, and does not need to be corrected.

According to one embodiment, as shown on FIG. 9 in relation to the embodiment of FIG. 4, and on FIG. 10 in relation to the embodiment of FIG. 5, respectively, the window 13 may be displayed adjacent to the window 9, enabling the user to simultaneously view the recommended dose and the dispensed dose.

After the dispensing was performed, and the window 13 is no longer displayed, dispensed drug information may still be available to the user through menu navigation.

According to some embodiments, actually dispensed drug information is not displayed live during or after drug dispensing, and is available after drug dispensing through menu navigation only.

While exemplary embodiment of the invention has been described with reference to two main embodiments, it will be understood by those skilled in the art that various changes, omissions and/or additions may be made, and equivalents may be substituted for elements thereof without departing from the spirit and scope of the invention. In addition, many modifications may be made to adapt a particular situation or material to the teachings of the invention without departing from the scope thereof. Therefore, it is intended that the invention is not limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

LIST OF REFERENCE SIGNS

1: drug dosage system
2: sensing system
3: terminal
4: drug dispensing device
5: container
6: dispensing system
7: setting system
8: display
9: window
10: window close button
11: reminder button
12: substitute window
13: window
14: needle
15: plunger
16: window
17: data communication device
18: caps
19: seal
20: "Amend" button
21: "Validation" button
22: Memory
23: Processor
24: Dose determination module
25: Security module
26: Notification module
27: Communication module
28: Query module
29: Input module
30: Output module

The invention claimed is:

1. A computerized system for the determination of a drug dosage to be applied to a user, wherein the computerized system comprises:
a memory storing data comprising at least time-based user metabolite data,
a processor comprising:

a dose determination module adapted to determine a possible drug dosage based on said data and at least one rule associating possible dosages and data, a security module adapted to determine whether said time-based user metabolite data triggers a security threshold, and a notification module adapted to, when the security module determines that the security threshold is triggered, issue a user notification comprising at least said possible dosage, and a user interface adapted to interact with the user, comprising:

an output module adapted to provide said user notification to the user, an input module adapted to receive information from the user regarding the user notification, and a communication module adapted to receive drug dosage data from a drug dispensing device, wherein the notification module is adapted to allow the user to acknowledge the user notification through the input module, wherein said acknowledgement dismisses the user notification from the user interface independently of said received drug dosage data, and wherein the communication module remains adapted to receive said drug dosage data from the drug dispensing device after the user notification has been dismissed.

2. The computerized system according to claim 1, wherein the notification module is adapted to allow the user to acknowledge the user notification through the input module even after the communication module receives drug dosage data associated with the user notification.

3. The computerized system according to claim 1, wherein the notification module is adapted to issue said user notification together with an actuatable window close button, and wherein notification acknowledgement comprises detecting actuation of said window close button.

4. The computerized system according to claim 1, wherein the notification module is adapted to issue said user notification together with an actuatable reminder button adapted to, upon actuation, trigger a later notification, and wherein notification acknowledgement comprises detecting actuation of said reminder button.

5. The computerized system according to claim 4, wherein the notification module is adapted, upon actuation of the reminder button, to control display of a substitute window bearing said possible drug dosage.

6. The computerized system according to claim 1, wherein the processor further comprises a query module adapted, when actuated by the user, to provide the user with the most recently possible drug dosage data.

7. A computerized method for the determination of a drug dosage to be applied to a user, wherein the computerized method comprises:

determining, by a dose determination module of a processor, possible drug dosage based on data contained in a memory and at least one rule associating possible dosages and data, determining, by a security module of the processor, whether said time-based user metabolite data triggers a security threshold, when the security module determines that the security threshold is triggered, issuing, by a notification module of the processor, a user notification comprising at least said possible dosage, providing, by an output module of a user interface adapted to interact with the user, said user notification to the user, receiving, by an input module of the user interface, information from the user regarding the user notification, and receiving, by a communication module of the user interface, drug dosage data from a drug dispenser, wherein the notification module allows the user to acknowledge the user notification through the input module, wherein said acknowledgement dismisses the user notification from the user interface independently of said received drug dosage data, and wherein the communication module remains adapted to receive said drug dosage data from the drug dispensing device after the user notification has been dismissed.

8. A computer software comprising instructions which, when the program is executed by a computer, cause the computer to carry out the method of claim 7.

* * * * *